United States Patent [19]

Woodard et al.

[11] Patent Number: 5,693,785
[45] Date of Patent: *Dec. 2, 1997

[54] PURIFICATION OF DNA ON HYDROXYLATED SILICAS

[75] Inventors: Daniel Lee Woodard, Raleigh, N.C.; Adriann Howard Walters, Baltimore, Md.; James Arthur Down, Cary, N.C.

[73] Assignee: Becton, Dickinson and Company, Franklin Lakes, N.J.

[*] Notice: The term of this patent shall not extend beyond the expiration date of Pat. No. 5,342,931.

[21] Appl. No.: 340,780

[22] Filed: Nov. 17, 1994

Related U.S. Application Data

[60] Continuation of Ser. No. 248,790, May 25, 1994, abandoned, which is a division of Ser. No. 051,596, Apr. 23, 1993, Pat. No. 5,342,931, which is a continuation of Ser. No. 835,179, Feb. 13, 1992, abandoned.

[51] Int. Cl.$^6$ .......................... C12P 19/34; C07H 21/00; C07H 21/04
[52] U.S. Cl. .................. 536/25.4; 435/91.1; 435/975; 423/335
[58] Field of Search .................. 536/25.4; 423/332, 423/334, 335; 252/89.1, 135; 435/91.1, 975

[56] References Cited

U.S. PATENT DOCUMENTS

| | | | |
|---|---|---|---|
| 4,310,496 | 1/1982 | Achenbach et al. | 423/118 |
| 4,822,681 | 4/1989 | Schossler et al. | 428/405 |
| 4,833,239 | 5/1989 | DeBonville et al. | 536/25.41 |
| 4,900,677 | 2/1990 | Hewitt | 435/259 |
| 4,921,952 | 5/1990 | Longmire et al. | 536/25.41 |
| 4,923,978 | 5/1990 | McCormick | 536/25.4 |
| 5,075,430 | 12/1991 | Little | 536/25.41 |
| 5,106,966 | 4/1992 | Thomas et al. | 536/25.4 |
| 5,155,018 | 10/1992 | Gillespie et al. | 536/25.4 |
| 5,175,271 | 12/1992 | Thomas et al. | 536/26.13 |
| 5,234,809 | 8/1993 | Boom et al. | 536/25.4 |

FOREIGN PATENT DOCUMENTS 0 555 798 A1   8/1993   European Pat. Off.
2074892 A      11/1981  United Kingdom.
WO91/00924     1/1991   WIPO.

OTHER PUBLICATIONS

R. Boom, et al. "Rapid and Simple Method for Purification of Nucleic Acids" *J. Clin. Micro.* 28:495–503 (1990) month not available.

M. A. Marko, et al. "A Procedure for the Large–Scale Isolation of Highly Purified Plasmid DNA Using Alkaline Extraction and Binding to Glass Powder" *Anal. Biochem.* 121:382–287 (1982) month not available.

E. H. Willis, et al. "Prep–A–Gene™: A Superior Matrix for the Purification of DNA and DNA Fragments" *Bio Techniques* 9:92–99 (1990) month not available.

S. C. Chow, et al. "Quantitation of DNA Fragmentation Using Fiberglass Filters" *Anal. Biochem.* 183:42–45 (1989) month not available.

R. M. McCormick "A Solid–Phase Extraction Procedure for DNA Purification" *Anal. Biochem.* 181:66–74 (1989) month not available.

L. H. Lutze, et al. "A quick and efficient method for the recovery of plasmid or viral DNA from mammalian cells" *Nucl. Acids Res.* 18:6150 (1990) month not available.

B. Vogelstein, et al. "Preparative and analytical purification of DNA from agarose" *Proc. Natl. Acad. Sci. USA* 76:615–619 (1979) month not available.

Chemical Abstracts, vol.101, No. 14, Oct., 1984, Abstr. No. 121949d, Mitsusio et al. Kochi Daigaku Gakujutsu Kenkyu Hokoku Shizen Kagaku 32:321–325, 1983.

Chemical Abstracts, vol. 80, No. 4, Jan. 1974, Abstr. No. 16767t, Bertorelli et al. Fr. Demande 2,157,943, Jul. 1973.

*Primary Examiner*—Gary L. Kunz
*Attorney, Agent, or Firm*—Donna R. Fugit, Ph.

[57] ABSTRACT

Compositions and processes for isolation or purification of DNA are provided. The compositions are hydroxylated silica polymers produced by reacting silicon dioxide with an alkaline solution, followed by acidification. The hydroxylated silicas produced by this process can be used to bind DNA in aqueous solutions, without the need for binding reagents such as alcohols or chaotropes. The bound DNA may then be separated from the solution and eluted into water or a buffer by heating.

19 Claims, No Drawings

PURIFICATION OF DNA ON HYDROXYLATED SILICAS

This application is a continuation of application Ser. No. 08/248,790, filed May 25, 1994, now abandoned, which is a division of Ser. No. 051,596 filed Apr. 23, 1993 U.S. Pat. No. 5,342,931, issued Aug. 30, 1994, which is a continuation of application Ser. No. 07/835,179, filed Feb. 13, 1992, abandoned.

FIELD OF THE INVENTION

The invention pertains to the field of isolation and purification of deoxyribonucleic acids (DNA). In particular, the invention relates to materials and methods for purification of DNA.

BACKGROUND OF THE INVENTION

A wide range of technologies involve the use of deoxyribonucleic acids (DNA) in a variety of forms. For example, advances in recombinant DNA technology continually require the use of DNA in the form of probes, genomic DNA and plasmid DNA. Advances in diagnostics also utilize DNA in a variety of ways. For example, DNA probes are routinely used for detection and diagnosis of human pathogens, detection of genetic disorders and detection of food contaminants. DNA probes are also routinely used for locating, identifying and isolating DNAs of interest for genetic mapping, cloning and recombinant gene expression. In many instances, the DNA of interest is available only in extremely small amounts, and isolation and purification procedures can be laborious, inefficient and time-consuming. Conventional DNA purification protocols often involve the use of caustic, toxic and/or flammable chemicals, usually high concentrations of chaotropic salts or other chemical binding reagents such as alcohols.

There are numerous protocols for purifying DNA. U.S. Pat. No. 4,923,978 discloses a process for purifying DNA in which a solution of protein and DNA is passed over a solid support material having a high concentration of mildly acidic surface hydroxyl groups. This increases the affinity of the material for proteins and reduces its affinity for polyanions such as nucleic acids, i.e., the protein is bound and the DNA is not. U.S. Pat. No. 4,935,342 discloses purification of DNA by selective binding of DNA to an anion exchanger with subsequent elution. U.S. Pat. No. 4,946,952 discloses DNA isolation by precipitation with water-soluble ketones. A DNA purification procedure using chaotropes and dialyzed DNA is disclosed in U.S. Pat. No. 4,900,677.

These conventional protocols result in isolated or purified DNA, but traces of the binding reagent may carry through the purification process and remain in the final product. These chemical contaminants may interfere with further manipulation and analysis of the isolated DNA, for example by inhibition of enzymatic processes associated with amplification, hybridization, cloning, etc. Elimination of such binding reagents from the DNA isolation process therefore has the advantage of producing isolated DNA which may be used directly in subsequent enzymatic processes, without concern for the presence of potentially inhibitory substances. That is, DNA bound to the compounds of the present invention may be eluted directly into a buffer appropriate for a subsequent procedure simply by heating the hydroxylated silica with the bound DNA in the selected buffer (e.g., elution into amplification buffer for use in a nucleic acid amplification reaction, or into hybridization buffer for hybridization analysis). As an added advantage, the compounds of the invention allow recovery of increased amounts of DNA from the purification process, as compared to conventional silica binding matrices. In addition, chaotropic and alcohol binding reagents can be toxic, caustic, flammable, difficult to dispose of, and expensive. For these reasons, as well, it is desirable to eliminate them from DNA purification protocols.

As used herein, the term "nucleic acid reaction buffer" refers to buffers customarily used in nucleic acid reactions and manipulations which do not contain binding reagents. Examples include, but are not limited to, TRIS/EDTA (TE) buffers, TRIS/acetate/EDTA (TAE) buffers, TRIS/borate (TB) buffers, TRIS/borate/EDTA (TBE) buffers, potassium phosphate/DMSO/glycerol (KPDG) buffers, NaCl/TRIS/EDTA (STE) buffers, NaCl/TRIS/EDTA/TWEEN (STET) buffers, TRIS/NaCl/TWEEN (TNT) buffers, phosphate buffers, TRIS buffers, HEPES buffers, nucleic acid amplification buffers, nucleic acid hybridization buffers, and the like. Nucleic acid reaction buffers are to be distinguished from nucleic acid binding buffers, which contain binding reagents.

SUMMARY OF THE INVENTION

The invention provides hydroxylated silica polymers (silanol polymers) produced by reacting silicon dioxide ($SiO_2$) with alkali. The silanol polymers produced by this process can be used to purify or isolate DNA from aqueous solutions, without the need for the hazardous chemicals previously required as binding reagents for DNA purification. Nearly all of the DNA bound may be recovered using the inventive compounds, and the isolated DNA can be used directly in a wide variety of nucleic acid reactions and procedures, such as amplification, hybridization, cloning, etc.

The compounds of the invention bind DNA in a variety of aqueous solutions with reduced amounts of binding reagent or in the absence of a binding reagent. For example, certain compounds of the invention bind DNA in water or a nucleic acid reaction buffer. In addition, the bound DNA may be eluted from the hydroxylated silica polymer into water or an eluting solution simply by heating. The invention may be practiced with DNA from any source (e.g., bacteria, bacteriophage, clinical specimens, plants, animals, etc.), in any form (e.g., single-stranded, double-stranded, circular, or linear).

DETAILED DESCRIPTION OF THE INVENTION

The invention provides hydroxylated silicas, methods of making the hydroxylated silicas and methods for isolating or purifying DNA using the hydroxylated silicas. The hydroxylated silicas are polymeric molecules produced from $SiO_2$ by reaction with alkali, which serves to increase the surface hydroxyl groups as shown below:

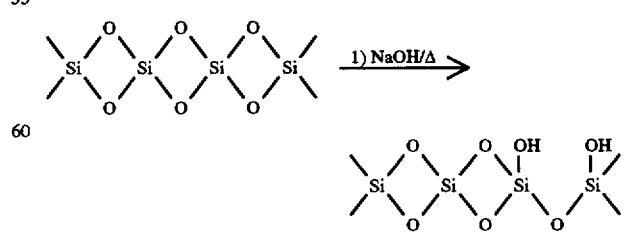

The sizes of the silanol polymer molecules produced in the reaction are probably variable, and may comprise 2 to about 100,000,000 repeating monomeric units of silicon dioxide. Most likely, the reaction produces a mixture of hydroxylated silica polymers, each comprising about 2–100,000 monomeric units.

To make the compositions of the invention, an alkaline solution is added to $SiO_2$ (e.g., in the form of diatoms, glass beads or glass fiber membranes). The method of making the hydroxylated silicas is not limited to any particular form of silica and may be used for hydroxylating any silicaceous material. The alkaline solution comprises NaOH, KOH, sodium hydride or a similar reagent which produces hydroxide ions in aqueous solution. The reagent which produces hydroxide ions in aqueous solution is referred to as an alkali. The counterion is not critical. The molar ratio of alkali to $SiO_2$ is about 0.1:1 to 10:1, preferably 2:1 to 10:1. Molar ratios of at least about 2:1 result in hydroxylated silicas which do not require binding reagents for binding of DNA. Molar ratios above 2:1 also produce hydroxylated silicas which bind DNA under native conditions, but dissolution of the $SiO_2$ increases as the proportion of alkali increases. Ratios of alkali:$SiO_2$ above 10:1 may result in complete dissolution of the particles or production of hydroxylated silica particles which are too small for efficient binding and isolation of DNA.

The suspension of $SiO_2$ in the alkaline solution is refluxed for a period of time sufficient to add hydroxide ions to the $SiO_2$ lattice. The time required for the reaction will vary depending on the concentration of hydroxide ion in the alkaline solution and the temperature of the reaction. Lower concentrations of hydroxide ion and/or lower temperatures require longer reaction times, whereas higher concentrations of hydroxide ion and/or higher temperatures reduce the reaction time. In general, refluxing the alkaline suspension for 48 hours is sufficient over a wide range of hydroxide ion concentrations. The final hydroxylated silica product is then recovered by filtering, washing and drying. Water, acetone, nucleic acid reaction buffers and the like are suitable washing reagents. The hydroxylated silica may be used for isolation or purification of DNA.

The DNA to be purified or isolated may be obtained in unpurified form from any source. Protocols for obtaining DNA from specimens such as serum, urine and bacterial cultures are well known. Similarly, methods for obtaining DNA from genomic libraries and the like are known. In general, these procedures result in a suspension of the DNA in solution with other, unwanted, molecules such as proteins and lipids. Once the DNA is obtained in such a solution, it is typically isolated and separated from the unwanted molecules by addition of a binding matrix. Conventional binding matrices are silica in the form of diatoms or glass. However, procedures using such conventional, unmodified silicas require high concentrations of chemical binding reagents (e.g., chaotropes or alcohols) in order for the DNA to bind to the matrix surface. Commonly used chaotropes include sodium iodide (NaI), urea, guanidinium hydrochloride, sodium perchlorate ($NaClO_4$), and potassium bromide (KBr).

The DNA isolation process of the invention does not require the presence of binding reagents for binding of DNA to the surface of the hydroxylated silica binding matrix. In contrast to the prior art, DNA may be bound to the inventive hydroxylated silicas in an aqueous solution at room temperature, without addition of chaotropes, alcohols or other similar binding reagents. The aqueous solution containing the DNA to be isolated may comprise water or a nucleic acid reaction buffer. The bound DNA may also be eluted from the hydroxylated silica by heating in water or a suitable nucleic acid reaction buffer, exemplified above. Although not required, reduced amounts of binding reagents such as chaotropes, alcohols and the like may be useful with certain compositions and in certain processes of the invention, as described below.

In general, the hydroxylated silicas of the invention are added to the solution containing the DNA to be isolated. Typically, the weight ratio of the hydroxylated silica to the DNA-containing solution is about 1:10 to 1:1. Binding of DNA becomes more efficient as the ratio approaches 1:1. A conventional binding buffer, containing a binding reagent, may also be added, but is not required. The DNA-containing solution is incubated with the hydroxylated silica to allow binding of DNA, typically at room temperature for about 1–20 minutes, preferably about 10 minutes. The mixture is then centrifuged to obtain a pellet of hydroxylated silica with bound DNA and a supernatant fraction. The supernatant is separated from the pellet and the pellet is washed with a wash solution, e.g., water, a nucleic acid reaction buffer or an alcohol solution. A preferred wash solution is 80% ethanol in 50 mM TRIS or 1X TAE. The DNA is then eluted from the hydroxylated silica by resuspending the pellet in an eluting solution (e.g., water or a nucleic acid reaction buffer) and heating at a temperature which is not destructive to DNA, preferably at about 37° C. The length of time required to obtain elution of the DNA can be determined empirically, and is not critical. For maximum yields, the elution step may be repeated.

The compositions of the invention may be assembled into a kit for convenient isolation or purification of DNA. The kit may include the hydroxylated silica in a container, either in dry form or in a suitable nucleic acid reaction buffer or water. Optionally, the kit may further include a container of a wash solution and/or a container of an eluting solution.

Specific embodiments of the invention are illustrated by the following experimental examples. The examples are not to be construed as limiting the invention defined by the appended claims. Various changes and modifications which would be apparent to skilled artisans are possible, and are intended to be included within the scope of the invention.

EXAMPLE 1

Acid washed CELITE 545 (diatoms—Alltech, Deerfield, Ill.) was hydroxylated using six different concentrations of NaOH to determine the effect of different degrees of hydroxylation on the ability of the reaction products to bind and elute DNA. The six hydroxylation reactions varied the amount of NaOH from 2.5 mM (100 mg) to 16.66 mM (666 mg) while keeping the amount of $SiO_2$ constant (0.5 g, 8.33 mM). The molar ratios of NaOH:$SiO_2$ corresponded to between 0.3 equivalents (eq) and 2.0 eq of NaOH. The NaOH was dissolved in 10 mL of water and added to the CELITE 545. The alkaline suspension was refluxed for 48 hours. The suspension was filtered to recover the solid reaction product. The reaction product was washed three times with 50 mL of water and three times with 50 mL of acetone. The hydroxylated silicas produced were evaluated by ESCA, SEM and FTIR and their DNA binding/elution capacities were evaluated in a DNA binding assay. The components of each reaction and the results of these analyses are shown in Table 1.

TABLE 1

| Conc. NaOH (mM) | SiO₂ Eq | OH Peak Height (Kubelka Munk) | O:Si*** | Particle Size** (μm) | DNA Binding |
|---|---|---|---|---|---|
| 0.00 | 0.0 | 0.006 | 2.20 | 100 | ++ 3.0 M |
| 2.50 | 0.3 | 0.020 | 2.40 | 2–14 | ++ 2.0 M |
| 4.20 | 0.5 | 0.022 | — | 2–6 | ++ 2.0 M |
| 5.83 | 0.7 | 0.023 | — | — | ++ 2.0 M |
| 8.33 | 1.0 | 0.069 | — | — | ++ 1.5 M |
| 12.5 | 1.5 | 0.059 | — | — | ++ 1.5 M |
| 16.66 | 2.0 | 0.040 | 3.20 | 2–3 | +++* |

++ Near complete elution of DNA across a portion of the NaClO₄ titration. Minimum concentration of NaClO₄ required for DNA binding and elution is noted.
+++ Near complete elution of DNA across the entire titration of NaClO₄.
*DNA binds in water at room temperature and is eluted at 37° C. in water.
**Determined from SEM.
***Determined for ESCA.

FTIR analysis was used to determine the extent of hydroxylation produced by each reaction. The height of the hydroxyl peak in the FTIR spectrum is proportional to the concentration of hydroxyl groups in the compound analyzed. The intensity of the hydroxyl peak of the unmodified diatoms (0.0 mM NaOH) was 0.006 Kubelka Munk units. This indicated a very low concentration of hydroxyl moieties on the diatom surface. The intensity of the hydroxyl peaks for the six reaction products was higher than for unmodified diatoms, and increased with increasing NaOH concentration. Hydroxylation of diatoms using the lowest three concentrations of NaOH resulted in an increase in intensity of 233% to 283% over unmodified diatoms. Diatoms hydroxylated with the three highest concentrations of NaOH had a hydroxyl peak intensity at least 666% of the hydroxyl peak of unmodified diatoms. Hydroxylation appeared to reach a maximum at 8.33 mM NaOH and then to decrease slightly at higher equivalencies. However, there was a general correlation between increasing hydroxyl peak intensity and reduced requirements for binding reagents to obtain near complete recovery of DNA. The size of the hydroxyl peak may be affected by atmospheric moisture or other sources of water. Although extreme care was taken to minimize the effect of extraneous water, discrepancies in the data, such as the hydroxyl peak maximum occurring at a point lower than expected, may be due to this factor. Surface area may also affect hydroxyl peak intensity due to scattering of light. SEM data showed that the surface area of the modified diatoms may increase as NaOH concentration in the reaction increases.

ESCA analysis was used to determine the percentage of each atom occurring on the surface of the reaction product. This data was used to determine the O:Si ratio, which is an indication of the extent of hydroxylation on the surface where DNA binding occurs. An increase in the O:Si ratio reflects addition of oxygen atoms to the surface of the diatoms (see the reaction scheme, above). Hydrogen atoms are not determined in ESCA analysis. Unmodified diatoms and diatoms hydroxylated using 2.50 mM and 16.666 mM NaOH were analyzed. The unmodified diatoms contained primarily $SiO_2$, O:Si=2.20, with 26.02% impurities from carbon, nitrogen and sodium. These impurities may be introduced from the water used to prepare the sample for ESCA, but they are water soluble and do not influence the outcome of the DNA binding assay. Further, the levels and types of impurities in all three samples were similar, whereas the DNA binding and elution properties were significantly different.

Diatoms hydroxylated using 2.50 mM NaOH had O:Si=2.40, indicating that a low level of hydroxylation had occurred. Diatoms hydroxylated using 16.66 mM NaOH had O:Si=3.20, indicating increased hydroxylation as compared to 2.50 mM NaOH. Increased hydroxylation with increasing concentrations of NaOH corroborates the Sn2 nucleophilic reaction scheme set forth above, as the rate of a nucleophilic reaction depends on the concentration of the nucleophile (NaOH). There was also a strong correlation between increased O:Si ratio and increased recovery of DNA with reduced concentrations of chaotrope in the DNA binding assay.

SEM analysis was used to determine the particle size of the reaction products. As shown in Table 1, the size of the particle decreased as the concentration of NaOH increased. Even the unmodified diatoms presented a large surfaced area, due to their irregular shape. As the concentration of NaOH in the reaction increased, the particles partially dissolved and became reduced in size, increasing the surface area for DNA binding. Dissolution is most likely the result of the alkali splitting the $SiO_2$ lattice on the surface of the diatom. The data showed a strong correlation between the increased capacity for DNA binding/elution and increased dissolution of the diatoms. Although dissolution and increased surface area may contribute to an increased capacity for DNA binding in the compositions of the invention, it is the addition of the hydroxyl groups which is believed to be most important for providing the new properties of these compounds, i.e., the ability to bind DNA in the absence of binding reagents.

The hydroxylated diatoms were evaluated for their ability to bind and elute DNA. $NaClO_4$ was used as a binding reagent to induce binding to the solid phase. For each hydroxylated silica tested, a solution of 31 μg of λDNA in 50 μL 50 mM TRIS, pH 7.0 was prepared. The hydroxylated silica (20 μL) was added to the DNA solution with 400 μL of one of six concentrations of $NaClO_4$ binding buffer (1.0M, 1.5M, 2.0M, 2.5M, 3.0M and 3.5M). The mixtures were incubated for 10 minutes at room temperature. After centrifugation and removal of the supernatant, the pellets were washed twice with 80% ethanol/50 mM TRIS, pH 7.0. DNA was eluted from the washed pellet in 20 μL of water at 37° C. for 10 minutes. The binding matrix was separated by centrifugation, and the supernatant containing the eluted DNA was removed to a separate tube. The elution was repeated, and the second supernatant was combined with the first. The eluted DNA was electrophoresed on a 1% agarose gel, stained with ethidium bromide and photographed over UV light. The amounts of DNA recovered were compared visually.

SUPER FINE SUPER FLOSS CELITE (SFSFC, Manville) was used as the unmodified silica control, and gave nearly complete recovery of DNA when a minimum of about 2.5–3.0M $NaClO_4$ was used as the binding buffer. DNA was not recovered from SFSFC when lower concentrations of $NaClO_4$ were used for binding or in the absence of chaotrope. SFSFC was selected as the unmodified silica control binding matrix because in binding studies comparing SFSFC and the PREP-A-GENE DNA purification kit (also an unmodified silica binding matrix, Bio-Rad, Richmond, Calif.) PKEP-A-GENE required slightly higher concentrations of chaotrope for binding (3M $NaClO_4$). Binding and elution of DNA on the hydroxylated diatoms was compared to that of SFSFC at 3.0M $NaClO_4$. The results showed that the minimum concentration of chaotrope in the binding buffer required to obtain near complete recovery of DNA decreased as the molar ratio of $NaOH:SiO_2$ in the reaction increased (See Table 1). When 16.66 mM NaOH (2 eq) was used in the hydroxylation reaction, the reaction product provided nearly complete elution of DNA at 1.0M $NaClO_4$—the lowest concentration of chaotrope tested in this assay.

The hydroxylated silica produced by reaction with 2 eq NaOH was then further tested for its ability to bind and elute DNA in the absence of a binding reagent. There was nearly complete binding of DNA to this product in water at room temperature. The recovery of the bound DNA in water at 37° C. was also nearly complete. This illustrates that as the surface concentration of hydroxyl groups (O:Si) increases and the particle size decreases, the minimum binding reagent concentration required for isolation of DNA also decreases. As the mole ratio of alkali:silica in the reaction reaches 2.0 eq, a hydroxylated silica product which allows binding and recovery of DNA under native conditions (i.e., in the absence of a binding reagent) is produced.

EXAMPLE 2

To demonstrate that the invention is applicable to silicacious compounds in general, acid washed glass beads (106 µm, Sigma) were refluxed with 2.0 eq sodium hydroxide for 48 hours. FTIR analysis of the unmodified glass beads showed a small hydroxyl peak (intensity 0.04 Kubelka-Munk) indicating a low concentration of surface hydroxyl groups. However, in the hydroxylated glass beads the hydroxyl peak was increased (intensity 0.18 Kubelka-Munk). This represents a 450% increase in hydroxyl peak intensity as compared to unmodified glass beads. ESCA analysis showed an O:Si ratio of 2.06 for the unmodified glass beads and 2.26 for the hydroxylated glass beads, indicating that hydroxylation had occurred on the bead surface. Impurities detected were similar in the modified and unmodified beads and did not affect the DNA binding and elution capacities of the material.

The results of ESCA and FTIK analysis suggested that hydroxylation of glass beads had taken place to a lesser extent than hydroxylation of diatoms under the same reaction conditions. This may be due to the lesser surface area of the glass beads, which are smoother and rounder than the rough, irregularly shaped diatoms. Less surface area on the glass beads may provide fewer reactive sites for hydroxylation and therefore a slower reaction rate. This is consistent with the Sn2 type of reaction believed to be occurring, as the rates of such reactions are dependent on the concentration of the substrate as well as the concentration of the nucleophile.

The DNA binding and eluting capacity of the hydroxylated glass beads was compared to unmodified glass beads, comparing the quantity of DNA recovered from samples containing known quantities of DNA. Seven concentrations of DNA were tested, ranging from 1 µg to 30 µg in 50 µL TRIS-HCl pH 8. Twenty µL of hydroxylated or unmodified glass beads (1:5 w/w in sterile MilliQ water) were added along with 300 µL of 6M $NaClO_4$. This mixture was incubated for 10 minutes at room temperature and centrifuged. The supernatant was removed and the pellet was washed twice with 50 µL of 50/50 ethanol/10 mM TRIS-HCl pH 8, centrifuging and discarding the supernatant between washes. Twenty µL of sterile MilliQ water were added to the final pellet and the mixture was incubated for 10 minutes at 37° C. to elute the bound DNA. After centrifugation, the supernatant was removed, the elution was repeated and the second supernatant was combined with the first. The combined supernatants were analyzed by gel electrophoresis on a 1% agarose gel. The amounts of DNA recovered were determined by densitometry.

The hydroxylareal glass beads gave a consistently higher recovery of DNA than the unmodified glass beads. For 30 µg of DNA, twice the amount of DNA was recovered using hydroxylated glass beads as was recovered using unmodified glass beads. Similar or better recovery was obtained with the other DNA concentrations tested. There was a linear increase in the amount of DNA recovered up to 20 µg using the hydroxylated glass beads, followed by a >100% increase in the amount of DNA recovered at 25 µg of DNA. The recovery rate leveled off above 25 µg of DNA, indicating that the saturation point had been reached for the concentration of beads tested. A similar saturation effect was observed with the unmodified glass beads.

The hydroxylated glass beads were also tested and found to bind DNA under native conditions, in the absence of a binding reagent. Binding and recovery was comparable to binding and recovery from diatoms hydroxylated using 2 eq. NaOH. This result was unexpected, as the hydroxylated glass beads are larger and appear to have a lower concentration of hydroxyl groups in spite of the equivalent reaction conditions. However, the glass beads are convened to a powder during the reaction, indicating a potentially larger increase in surface area. The increase in surface area may at least partially compensate for reduced hydroxylation.

What is claimed is:

1. A process for purifying DNA which comprises:
   a) binding the DNA to an hydroxylated silicaceous material in the presence of water or a nucleic acid reaction buffer, wherein the hydroxylated silicaceous material is produced by a process comprising
      i) providing an aqueous solution of an alkali,
      ii) mixing the aqueous solution of the alkali with the silicaceous material at a molar ratio of alkali to silicaceous material of about 2:1 to 10:1,
      iii) refluxing the mixture for a period of time sufficient to hydroxylate the silicaceous material, and
      iv) acidifying the mixture such that protonation of the hydroxylated silicaceous material is completed;
   b) separating and washing the hydroxylated silicaceous material and the DNA bound thereto, and:
   c) eluting the DNA from the hydroxylated silicaceous material in a heated nucleic acid reaction buffer or in heated water.

2. The process of claim 1 wherein the DNA is bound to the hydroxylated silica compound in a buffer selected from the group consisting of TRIS/EDTA, TRIS/borate, TRIS/borate/EDTA, TRIS/acetate/EDTA, potassium phosphate/DMSO/glycerol, NaCl/TRIS/EDTA, NaCl/TRIS/EDTA/TWEEN, TRIS/NaCl/TWEEN, phosphate buffers, TRIS buffers, HEPES buffers, nucleic acid amplification buffers and nucleic acid hybridization buffers.

3. The process of claim 1 wherein the weight ratio of hydroxylated silica compound to water or nucleic acid reaction buffer is 1:10 to 1:1.

4. The process of claim 1 wherein the DNA is bound to the hydroxylated silica compound for 1–20 minutes at room temperature.

5. The process of claim 1 wherein the DNA is eluted in a heated buffer selected from the group consisting of TRIS/EDTA, TRIS/borate, TRIS/borate/EDTA, TRIS/acetate/EDTA, potassium phosphate/DMSO/glycerol, NaCl/TRIS/EDTA, NaCl/TRIS/EDTA/TWEEN, TRIS/NaCl/TWEEN, phosphate buffers, TRIS buffers, HEPES buffers, nucleic acid amplification buffers and nucleic acid hybridization buffers.

6. The process of claim 5 wherein the DNA is eluted at 37° C.

7. An hydroxylated silicaceous material produced by a process comprising:

a) providing an aqueous solution of an alkali, b) mixing the aqueous solution of the alkali with the silicaceous material at a molar ratio of alkali to silicaceous material of about 2:1 to 10:1, c) refluxing the mixture for a period of time sufficient to hydroxylate the silicaceous material, and d) acidifying the mixture such that protonation of the hydroxylated silicaceous material is completed.

8. The silicaceous material of claim 7 produced by a process wherein the alkali is selected from the group consisting of sodium hydroxide and potassium hydroxide.

9. The silicaceous material of claim 8 produced by a process wherein the mixture is refluxed for about 48 hours.

10. The silicaceous material of claim 9 produced by a process wherein the mixture is acidified by addition of an acid selected from the group consisting of hydrochloric acid, nitric acid, sulfuric acid and acetic acid.

11. The silicaceous material of claim 10 produced by a process wherein the mixture is acidified to about pH 4–5.

12. A process for producing an hydroxylated silicaceous material comprising:

a) providing an aqueous solution of an alkali, b) mixing the aqueous solution of the alkali with the silicaceous material at a molar ratio of alkali to silicaceous material of about 2:1 to 10:1, c) refluxing the mixture for a period of time sufficient to hydroxylate the the silicaceous material;

d) acidifying the mixture such that protonation of the hydroxylated silicaceous material is completed, and;

e) recovering the hydroxylated silicaceous material.

13. The process of claim 12 wherein the alkali is selected from the group consisting of sodiium hydroxide and potassium hydroxide.

14. The process of claim 13 wherein the mixture is refluxed for about 48 hours.

15. The process of claim 12 wherein the mixture is acidified by addition of an acid selected from the group consisting of hydrochloric acid, nitric acid, sulfuric acid and acetic acid.

16. The process of claim 15 wherein the mixture is acidified to about pH 4–5.

17. A kit for purifying DNA comprising:

a) an hydroxylated silica compound produced by a process comprising i) providing an aqueous solution of an alkali, ii) mixing the aqueous solution of the alkali with $SiO_2$ at a molar ratio of alkali to $SiO_2$ of about 2:1 to 10:1, iii) refluxing the mixture for a period of time sufficient for addition of hydroxide ions to the $SiO_2$, and iv) acidifying the mixture such that the hydroxylated silica compound is produced, and;

b) optionally, an eluting solution selected from the group consisting of water and nucleic acid reaction buffers.

18. The kit of claim 17 wherein the hydroxylareal silica compound is provided in a nucleic acid reaction buffer or water.

19. The kit of claim 17 further comprising a wash solution selected from the group consisting of water, nucleic acid reaction buffers and alcohol solutions.

* * * * *